(12) United States Patent
Truitt et al.

(10) Patent No.: US 6,644,311 B1
(45) Date of Patent: Nov. 11, 2003

(54) MONITORING FLUID FLOW IN A PRESSURE SUPPORT SYSTEM

(75) Inventors: Patrick W. Truitt, Pittsburgh, PA (US); Winslow K. Duff, Export, PA (US)

(73) Assignee: Respironics, Inc., Murrysville, PA (US)

( * ) Notice: Subject to any disclaimer, the term of this patent is extended or adjusted under 35 U.S.C. 154(b) by 0 days.

(21) Appl. No.: 10/027,487

(22) Filed: Dec. 19, 2001

Related U.S. Application Data

(60) Provisional application No. 60/270,490, filed on Feb. 21, 2001.

(51) Int. Cl.$^7$ .............................................. A61M 16/00
(52) U.S. Cl. ............................ 128/204.22; 128/204.18; 128/204.21
(58) Field of Search ................. 128/204.18, 204.21, 128/204.23, 202.22, 204.22, 205.23, 202.18, 202.19

(56) References Cited

U.S. PATENT DOCUMENTS

| | | | | |
|---|---|---|---|---|
| 5,540,220 A | * | 7/1996 | Gropper et al. ........ | 128/204.23 |
| 5,572,993 A | * | 11/1996 | Kurome et al. ........ | 128/204.23 |
| 5,645,054 A | * | 7/1997 | Cotner et al. .......... | 128/204.23 |
| 5,875,783 A | * | 3/1999 | Kullik ................... | 128/204.18 |
| 6,123,074 A | * | 9/2000 | Hete et al. ............. | 128/205.11 |
| 6,152,134 A | * | 11/2000 | Webber et al. ......... | 128/205.24 |
| 6,182,657 B1 | * | 2/2001 | Brydon et al. ......... | 128/205.24 |
| 6,216,691 B1 | * | 4/2001 | Kenyon et al. ........ | 128/205.18 |
| 6,299,581 B1 | * | 10/2001 | Rapoport et al. .......... 600/484 |
| 6,349,724 B1 | * | 2/2002 | Burton et al. .......... | 128/204.18 |
| 6,360,741 B2 | * | 3/2002 | Truschel ................ | 128/202.22 |
| 6,367,474 B1 | * | 4/2002 | Berthon-Jones et al. ...................... | 128/204.23 |
| 6,397,841 B1 | * | 6/2002 | Kenyon et al. ........ | 128/202.27 |
| 6,401,713 B1 | * | 6/2002 | Hill et al. .............. | 128/204.21 |
| 6,467,477 B1 | * | 10/2002 | Frank et al. ........... | 128/203.23 |
| 6,484,719 B1 | * | 11/2002 | Berthon-Jones ........ | 128/204.23 |

* cited by examiner

*Primary Examiner*—Weilun Lo
*Assistant Examiner*—Mital Patel
(74) *Attorney, Agent, or Firm*—Michael W. Haas

(57) ABSTRACT

The present invention pertains to a pressure support system in which a flow or volume of gas is measured without using a dedicated flow element used in a conventional flow meter. Instead, the present invention provides a tortuous gas flow path in which a pressure differential is created between two points in the tortuous path. This pressure differential created by the gas flow path provides the necessary pressure drop for measuring the gas flow and/or gas volume passing through the pressure support system.

26 Claims, 4 Drawing Sheets

MONITORING FLUID FLOW IN A PRESSURE SUPPORT SYSTEM

CROSS-REFERENCE TO RELATED APPLICATIONS

This application claims priority under 35 U.S.C. §119(e) from provisional U.S. patent application No. 60/270,490 filed Feb. 21, 2001.

BACKGROUND OF THE INVENTION

1. Field of the Invention

The present invention pertains to a technique for measuring gas flow and/or volume in a pressure support system, and, more particularly, to a gas flow and/or volume measurement technique in which a pressure differential occurring between two points in a tortuous gas flow path in the pressure support system is used to measure the gas flow and/or gas volume passing through the tortuous gas flow path, thereby eliminating the need for a dedicated flow element in the gas flow path to create the pressure differential for flow/volume measurement purposes.

2. Description of the Related Art

Pressure support systems that provide a flow of gas to an airway of a patient at an elevated pressure via a patient circuit to treat a medical disorder are well known. For example, it is known to use a continuous positive airway pressure (CPAP) device to supply a constant positive pressure to the airway of a patient to treat obstructive sleep apnea (OSA) as well as other disorders. It is also known to provide a positive pressure therapy in which the pressure of gas delivered to the patient varies with the patient's breathing cycle, or varies with the patient's effort to increase the comfort to the patient, which is typically referred to as bi-level pressure support. It is further known to provide a positive pressure therapy in which the pressure provided to the patient changes based on the detected conditions of the patient, such as whether the patient is snoring or experiencing an apnea, hypopnea or upper airway resistance. This typically is referred to as an auto-titration mode of pressure support because the pressure support system automatically attempts to titrate the pressure support to suit the needs of the patient.

As shown in FIG. 1, a conventional pressure support system 10 typically includes a pressure generator 12, for example, a blower, piston, or bellows, that receives a supply of gas from a gas source, such as ambient atmosphere, as indicated by arrow A, and creates a flow of breathing gas, as indicated by arrows B, having a pressure greater than the ambient atmospheric pressure. A patient circuit 14, which is typically a flexible conduit, delivers the elevated pressure breathing gas to the airway of the patient. Typically, the patient circuit is a single limb conduit or lumen having one end coupled to the pressure generator and a patient interface device 16 coupled to the other end.

Patient interface device 16 connects patient circuit 14 with the airway of the patient so that the elevated pressure gas flow is delivered to the patient's airway. Examples of patient interface devices include a nasal mask, nasal and oral mask, full face mask, nasal cannula, oral mouthpiece, tracheal tube, endotracheal tube, or hood. A single limb patient circuit shown in FIG. 1 includes an exhalation port 18, also referred to as an exhalation vent, exhaust port, or exhaust vent, to allow gas, such as expired gas from the patient, to exhaust to atmosphere, as indicated by arrow C. Generally, exhaust vent 18 is located in patient circuit 14 near patient interface device 16 or in the patient interface device itself.

More sophisticated pressure support devices include a flow sensor 20, pressure sensor 22 or both that monitor the flow and/or pressure of gas passing in patient circuit 14. The flow information can also be used to determine the volume of gas passing through patient circuit 14. The information from flow sensor 20 and/or pressure sensor 22 is used, for example, to control the pressure or flow of gas provided to the patient, monitor the condition of the patient, monitor the usage of the pressure support device (patient compliance), or any combination thereof. FIG. 1 illustrates a flow sensor 20 and pressure sensor 22 downstream of pressure generator 12.

As shown in FIG. 2, which illustrates an example of a typical flow sensor, flow sensor 20 includes a conduit 24 having ends 26 and 28 so that gas can flow through the conduit, as indicated by arrow D. A flow element 30 is provided in conduit 24 between ends 26 and 28 to create a pressure drop ($\Delta P$) in the conduit. That is, flow element 30 causes a pressure difference $\Delta P$ between pressure $P_1$ and pressure $P_2$ so that $\Delta P = P_2 - P_1$.

In one type of conventional sensor, pressure differential $\Delta P$ is measured directly by a pressure sensor 32, which is connected to conduit 24 on each side of flow element 30 via ports 34 and 36. This pressure differential is used to calculate the flow of gas passing through conduit 24, which, in turn, is used to calculate the volume of gas flowing through conduit 24 over any given period of time.

In another type of conventional flow sensor, pressure differential $\Delta P$ is not measured directly. Instead, a conduit is coupled between ports 34 and 36. The pressure differential between these ports causes a sidestream flow of gas to flow through this conduit connecting ports 34 and 36. A mass flow sensor 32' is provided in place of pressure sensor 32 to measure the sidestream flow passing between ports 34 and 36. This sidestream flow is then used to calculate the flow of gas in conduit 24 and also the volume of gas flowing through conduit 24 over any given period of time.

The signal from flow sensor 20, whether from pressure sensor 32 or mass flow sensor 32', is provided to a controller 38 where it is used for the purposes noted above, such as to control the pressure or flow of gas provided to the patient or monitor the patient's usage of the medical device. One conventional pressure/flow control method involves providing a valve 40 in the patient circuit downstream of pressure generator 12 to exhaust a portion of the breathing gas output by the pressure generator through an exhaust conduit, as indicated by arrow E, thereby decreasing the pressure and flow delivered to the patient.

Another conventional pressure/flow control method involves controlling the operating speed of pressure generator 12, e.g., controlling the motor speed of a blower that is used to create a flow of gas so that the pressure generator outputs the gas at the desired rate or pressure without an additional pressure control valve. It is also known to use a combination of valve 40 and motor speed control to control the pressure or flow of breathing gas output to the patient.

Controller 38 receives the signals output from sensors 20 and 22 and controls the operation of valve 40, pressure generator 12, or a combination thereof in a feedback fashion based on these received signals. For example, in a simple CPAP device, controller 38 monitors the pressure or flow of breathing gas delivered to the patient and adjusts the pressure or flow in a feedback fashion to meet the desired prescription pressure level. In a more sophisticated bi-level pressure support system, where the pressure is greater during inspiration than during expiration, controller 38 receives the flow signal and the pressure signal from flow sensor 20 and pressure sensor 22, respectively, and uses this information to determine when the patient has transitioned from the inspiratory phase to the expiratory phase of the breathing cycle, or vice versa, to control the pressure accordingly. In the auto-titration mode of pressure support, where the flow of breathing gas and the pressure level thereof is controlled based on the conditions of the patient, these pressure and flow sensors, or other sensors, such as a microphone, are used to detect snoring, apneas, hypopneas, etc. The pressure and/or flow is then controlled to counteract or prevent these conditions.

An input/output device 42, such as a keypad, buttons, lights, LED or LCD display, and/or an audio device, is used to enter information and commands to the pressure support system and to display information. For example, an input device can be used to enter the operating pressure in a CPAP system, the inspiratory positive airway pressure (IPAP) and expiratory positive airway pressure (EPAP) in a bi-level system, and the maximum and minimum pressures and pressure change in an auto-titration system.

It can be appreciated that providing a conventional flow sensor in the pressure support system increases the complexity and cost of the device. This is so because the flow sensor must be manufactured and calibrated with a relatively high degree of precision to ensure an accurate output.

Others have attempted to avoid the use of a flow sensor altogether, for example, by monitoring the current or work performed by the pressure generator 12. As the patient breathes into patient circuit 14, the load on the pressure generator increases, this change in load can be detected and used to determine that the patient is breathing into the system. This monitoring technique, however, is relatively inaccurate, and, therefore, not suitable for quantitatively measuring the flow or volume of gas in the pressure support system, which is especially important in using the measured flow for triggering and cycling purposes.

SUMMARY OF THE INVENTION

It is, therefore, an object of the present invention to provide a pressure support system that overcomes the disadvantages associated with conventional pressure support systems. In particular, it is an object of the present invention to provide a pressure support system that allows for a relatively accurate flow or volume measurement of the gas passing therethrough, without the need for a dedicated flow element.

These objects are achieved, according to one embodiment of the present invention, by providing a pressure support system that includes a gas carrying conduit having a first end and a second end. Breathing gas from a gas source is received at the first end of the conduit. A pressure generator is provided at a first location along the conduit for generating a flow of breathing gas within the conduit. A first port is defined in the conduit at a second location, and a second port is defined in the conduit at a third location. The conduit is formed into a tortuous path between the second location and the third location so as to induce a pressure differential in the flow of breathing gas between the second location and the third location. In addition, a sensor associated with the first port and the second port measures a characteristic of the breathing gas in the conduit resulting from the pressure differential and outputs a signal indicative thereof. By making use of the pressure drop caused by the tortuous path, the need for a separate flow element found in conventional flow sensors is eliminated.

The present invention contemplates that the signal from the sensor can be used in the same manner as the signal from a conventional flow sensor. These uses include controlling the operation of the device, i.e., the pressure or flow delivered to the patient, and monitoring the usage of the device. The present invention further contemplates that the second and third locations, where the first and second ports are respectively provided, can be upstream or downstream of the pressure generator.

It is yet another object of the present invention to provide a method of providing pressure support that does not suffer from the disadvantages associated with conventional pressure support techniques and that can perform an accurate flow or volume measurement without a dedicated flow sensor. This object is achieved by providing a method that includes: (1) providing a gas carrying conduit having a first end adapted to receive breathing gas from a gas source and a second end, (2) generating a flow of breathing gas within the conduit via a pressure generator disposed at a first location along the conduit, and (3) providing a first port in the conduit at a second location and a second port in the conduit at a third location. The conduit is configured so as to define a tortuous path between the second location and the third location, thereby inducing a pressure differential in the flow of breathing gas between the second location and the third location. This process further includes measuring, via a sensor associated with the first port and the second port, a characteristic of the breathing gas in the conduit resulting from the pressure differential and outputting a signal indicative thereof. As noted above, this signal can be used for many purposes, and the first and second ports can be provided upstream or downstream of the pressure generating element.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE PRESENTLY PREFERRED EXEMPLARY EMBODIMENTS

Figure 1:
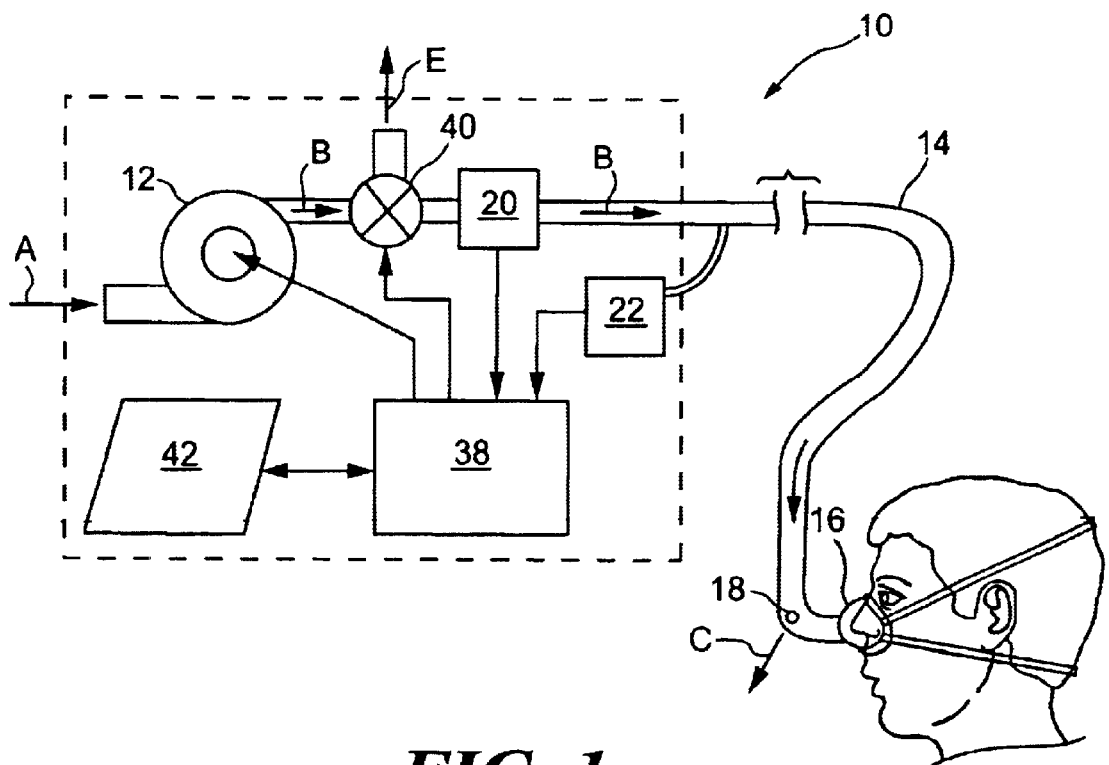
FIG. 1 is a schematic view of a conventional pressure support system.
Figure 2:
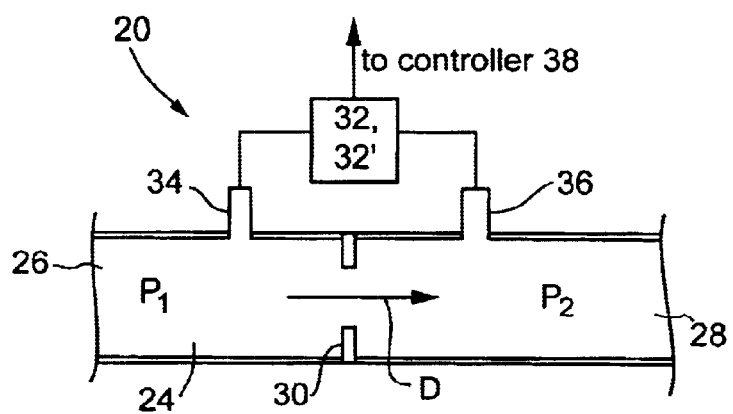
FIG. 2 is a schematic view of a conventional flow sensor used in a conventional pressure support system.

A pressure support system 50, according to the principles of the present invention, will now be described with reference to FIGS. 3–5. For simplicity of description, like elements in the description of the present invention shown in FIGS. 3–5 and in the description of the conventional pressure support system shown in FIG. 1 have like reference numbers.

Pressure support system 50 includes a pressure generator 12 in the form of a blower assembly 52 driven by a motor 54. An inlet of the blower is coupled to a first conduit 56 that communicates the inlet of the blower to a source of breathing gas for the pressure generator, such as ambient atmosphere. It is to be understood that other sources of gas can be used instead of, or in addition to, the air from the ambient atmosphere. For example, a supply of oxygen or an oxygen mixture can be provided as source of breathing gas. In addition, other types of pressure generators, such as a piston, bellows, or fan, can be provided for pressure generator 12. A housing 58 identified by the dashed line in FIG. 3 contains these elements of the pressure support system.

First conduit 56 defines a tortuous path, generally indicated by arrows F, from its first end, which in this embodiment is the ambient atmosphere, to its second end, which is at the inlet of pressure generator 12. Preferably, a noise dampening material 60, such as foam, is provided on the walls of the first conduit to absorb noise. In the illustrated exemplary embodiment, a filter 62 is provided at the inlet of the first conduit to prevent particulate matter from entering the blower assembly. Filter 62 also provides a sound dampening function so that the combination of the tortuous, baffled path defined by the first conduit and the sound dampening filter effectively function as a muffler for the pressure support system.

An outlet of pressure generator 12 is coupled to a second conduit 64 that communicates a flow of gas generated by the pressure generator, as indicated by arrow B, to patient circuit 14 for delivery to a patient. It can be appreciated that first conduit 56 and second conduit 64 together define a conduit traversing the pressure support system, with pressure generator 12 being provided at a first location along this overall conduit.

In the illustrated exemplary embodiment and as in a conventional pressure support system, valve 40 is provided in second conduit 64 for controlling the flow or pressure of the fluid delivered to the patient. In an exemplary embodiment of the present invention, valve 40 controls the pressure or the flow of breathing gas in the second conduit by exhausting gas from the second conduit, as indicated by arrow E. The exhaust gas diverted by valve 40 from second conduit 64 is either dispersed into the ambient atmosphere, as shown by arrow E in FIG. 3, reintroduced or re-circulated upstream of pressure generator 12, or a combination thereof. Another embodiment of the present invention contemplates that valve 40 controls the pressure or flow of gas in the second conduit by restricting the flow of gas from the pressure generator in addition to or instead of exhausting gas from the second conduit.

The present invention also contemplates changing the speed of motor 54 to control the pressure or rate of flow of gas generated by the blower assembly, either alone or in combination with pressure control via valve 40. Of course, if motor speed alone is used to regulate the pressure or flow of breathing gas provided to the patient, valve 40 is eliminated. Valve 40 and motor 54 are operated, as necessary, under the control of a controller 38.

Depending on the parameters to be monitored, pressure support system 50 can include a pressure sensor 22 in fluid communication with the fluid delivery system. In the illustrated embodiment, pressure sensor 22 monitors the pressure within second conduit 64, which can also be considered a portion of patient circuit 14 as the second conduit merges into the patient circuit where the patient circuit connects to the second conduit.

This pressure can be used to estimate the pressure at the patient, i.e., within patient interface device 16. Of course, the present invention also contemplates measuring the pressure at the patient, if desired, for example by providing a pressure pick-off port in or near the patient interface device. As is the case with a conventional pressure support system, the pressure signal output of pressure sensor 22 is provided to controller 38 for controlling the operation of the pressure support system, monitoring the operation of the system, or monitoring the patient, for example.

A flow/volume sensing system, generally indicated at 72, and which includes the tortuous path defined by first conduit 56, provides a flow signal to controller 68. As with the pressure signal, the flow signal output of flow sensing system 72 can be used to control the operation of the pressure support system, monitor the operation of the system, or monitor the patient.

Flow/volume sensing system 72 includes a first port 74 provided at a first location along first conduit 56 and a second port 76 provided at a second location along the first conduit. Unlike a conventional flow sensor, which requires a dedicated flow element to create a pressure differential in the conduit, flow/volume sensing system 72 uses the tortuous path to create pressure differential $\Delta P$. That is, the tortuous path provides a slight restriction in the flow of fluid therethrough, thereby causing a pressure difference $\Delta P$ to exist between pressure $P_1$ at port 74 and pressure $P_2$ at port 76. Of course, ports 74 and 76 must be spaced far enough apart along the tortuous path so that a measurable pressure differential exists between these ports. Stated another way, the tortuous path must be sufficiently winding or twisting between the two pressure ports so as to induce a sufficient pressure differential $\Delta P$. In addition to providing a pressure differential for fluid flow measurement purposes, the tortuous path at the inlet of pressure generator 12 also functions as muffler to dampen the noise resulting from operating the pressure generator.

A conventional pressure sensor 32 measures the pressure differential $\Delta P$ ($P_2 - P_1$) via ports 74 and 76, and provides a signal indicative of this pressure differential to controller 38 for calculating the flow and/or volume of gas passing through conduit 56. In another embodiment, a sidestream flow of gas is provided between ports 74 and 76, and a mass flow sensor 32' is provided in place of pressure sensor 32 to measure this sidestream flow. The output of flow sensor 32' is provided to controller 38 for calculating the flow and/or volume of gas passing through conduit 56.

It can be appreciated that pressure support system 50 can operate as any conventional pressure support system, such as CPAP device, a bi-level device, an auto-titration device, or a ventilator, depending on how controller 38 controls the operation of motor 54 and/or valve 40. For example, in a bi-level mode of operation, controller 38 receives flow signals and pressure signals from flow/volume sensing assembly 72 and pressure sensor 22, respectively, to distinguish between the inspiratory and expiratory phase of the patient's breathing cycle, as is known in the art, and delivers the appropriate IPAP and EPAP pressures by controlling valve 40, motor 54, or a combination thereof. It is to be further understood that other sensors can be provided to provide additional information to the controller.

Figure 4:
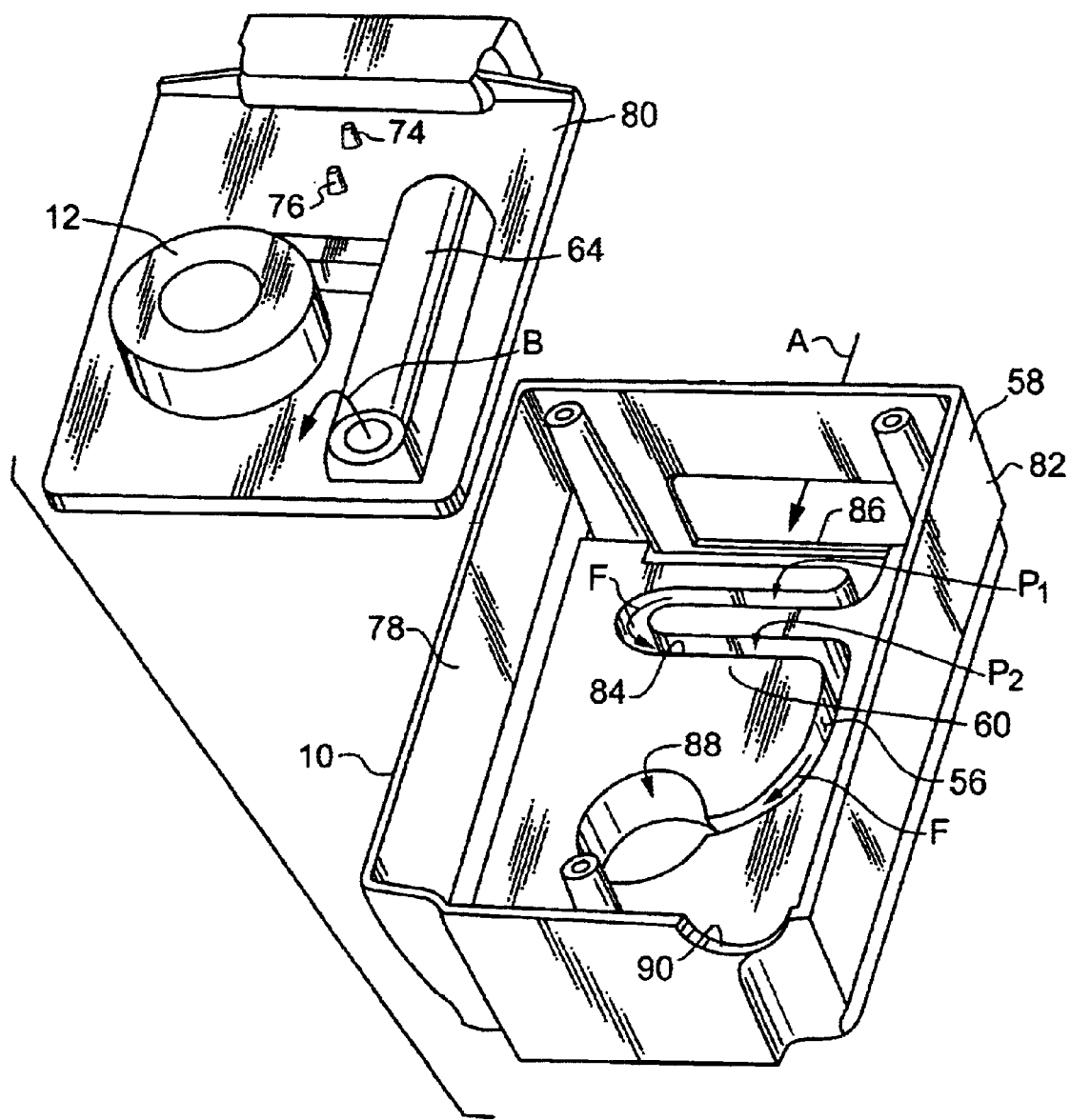
FIG. 4 is an exploded perspective view of a portion of the pressure support system of FIG. 3.
Figure 5:
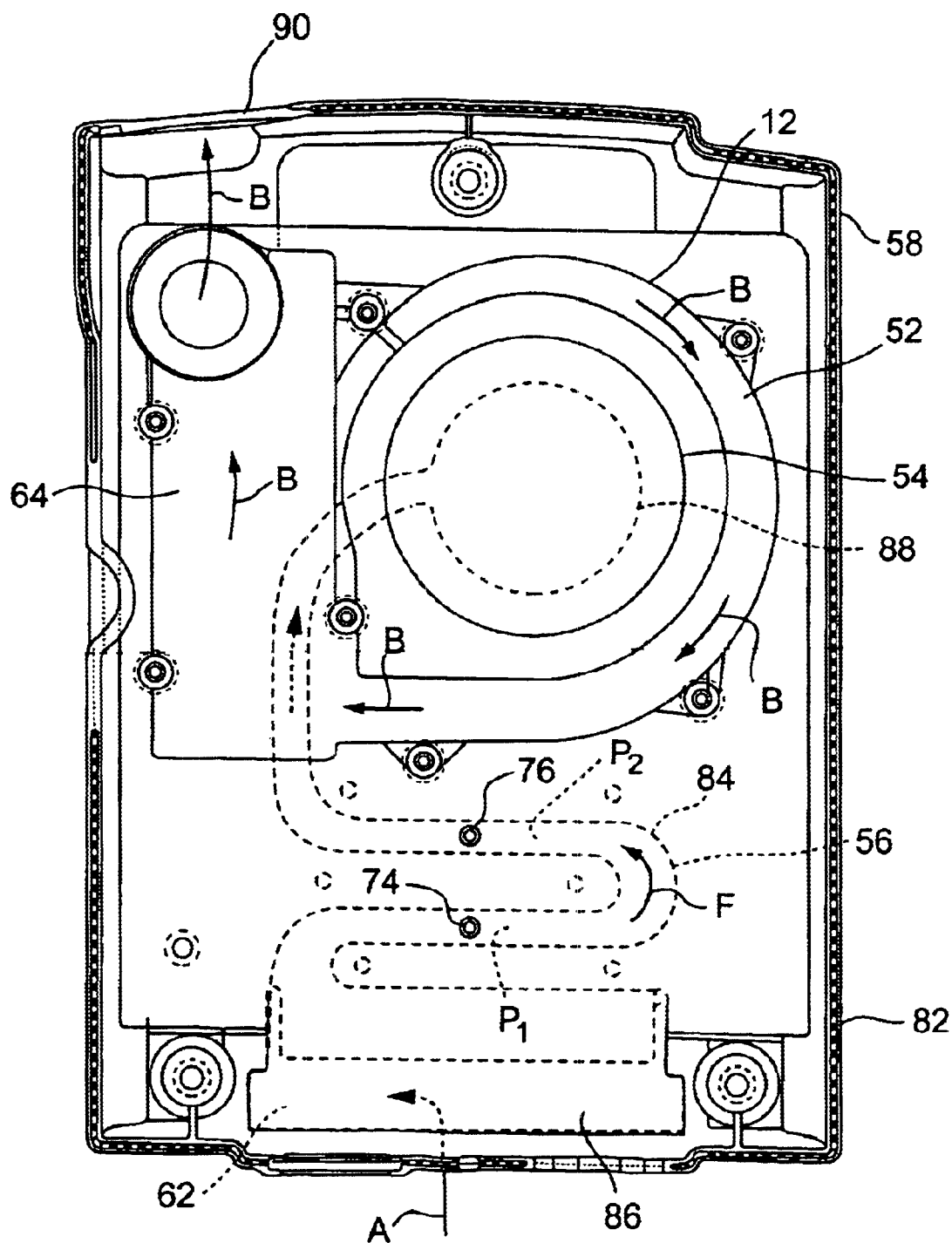
FIG. 5 is a top view of the portion of the pressure support system of FIG. 4 shown in an assembled configuration.

FIGS. 4 and 5 illustrate an exemplary configuration for flow/volume sensing assembly 72 in a pressure support system. It should be noted that FIGS. 4 and 5 only illustrate a portion of entire pressure support system and only a portion of the flow/volume sensing assembly. The primary purpose of FIGS. 4 and 5 is to illustrate an exemplary embodiment of first conduit 56 defining a tortuous path and to show how ports 74 and 76 are associated with the tortuous path in the flow/volume sensing assembly. Therefore, certain features of the pressure support system, such as a pressure sensor 32 or flow sensor 32', controller 38, and valve 40, are omitted for ease of illustration.

FIG. 4 illustrates, in exploded form, two members 78 and 80 that mate together to define first conduit 56. FIG. 5 is a plan view that illustrates these two members in an assembled configuration. In this embodiment, first member 78 includes a sound absorbent material 60, such as foam, that is attached in any conventional manner to a first housing component 82, which is preferable a hard plastic. First housing component 82 defines a portion of housing 58 for the pressure support system. A second housing component (not shown) mates with the first housing component to define the entire housing 58 for the system. In the illustrated exemplary embodiment, first housing component 82 functions as the base for the pressure support system.

A channel 84 is defined in material 60 for providing tortuous path F from an ambient atmosphere inlet 86 to an inlet of pressure generator 12. In this embodiment, a cutout area 88 in material 60 is also provided at the inlet of pressure generator 12. The fluid flow out of pressure generator 12, as indicated by arrows. B, is carried by second conduit 64 to an outlet 90 on housing 58, to which the patient circuit (not shown) connects. The specific components for connecting the second conduit to the patient circuit are omitted for ease of illustration and their specific configuration is not essential to a full understanding and appreciation of the present invention.

When first member 78 and second member 80 are assembled, the second member seals off the channel 84. In addition, ports 74 and 76, which are essentially holes defined in second member 80 to which a tubing can be attached, provide a fluid communication with a first portion and a second portion of first conduit 56. Although not shown in FIGS. 4 and 5, a pressure sensor or sidestream flow sensor is connected to ports 74 and 76, for example, via flexible tubing. Preferably, such sensors are mounted on a circuit board, which is, in turn, mounted above or on second member 80. The other components of the pressure support system, such as controller 38, can be mounted on the same circuit board or on other boards.

It is to be understood that the specific locations for ports 74 and 76, as well as the specific configuration, shape and size of the tortuous portion of first conduit 56 need not be as shown in FIGS. 4 and 5. On the contrary, the present invention contemplates other configurations and relative locations for these items, so long as a pressure differential ΔP is created that is sufficient to be measured by a pressure sensor or that causes a sufficient sidestream flow that can be measured by a flow sensor.

Figure 3:
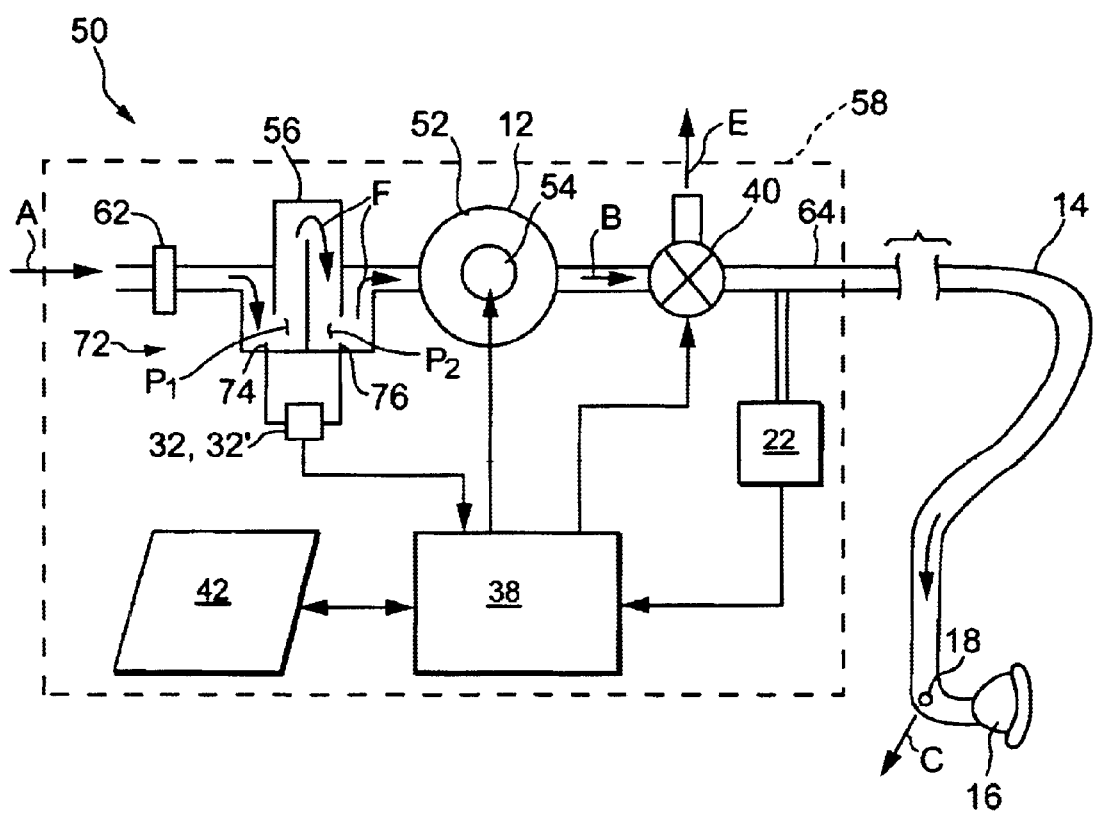
FIG. 3 is a schematic view of a pressure support system in accordance with the principles of the present invention.

In the embodiment illustrated in FIGS. 3–5, flow/volume sensing assembly 72 is provided upstream of pressure generator 12. However, the present invention also contemplates providing the flow/volume sensing assembly at other locations along the flow path through the pressure support system, in addition to or in place of the upstream location shown in these figures. For example, the present invention contemplates providing the tortuous flow path downstream of the pressure generator, yet within housing 58.

The present invention also contemplates providing the flow/volume sensing assembly at a modular attachment at the outlet of housing 58. For example, the tortuous path can be connected between an end of second conduit 64 and a corresponding end of patient circuit 14. In this embodiment, the flow/volume sensing assembly can operate in conjunction with controller 38, for example, by providing signals from sensor 32 or 32' to controller 38 via an external communication terminal. However, the present invention also contemplates that the flow/volume sensing assembly can operate as a standalone unit, for example, with its own power supply and input/output interface for displaying and/ or downloading the monitored information. As with the previous embodiments, such a configuration for flow/ volume sensing assembly provides an additional noise muffling capability to the existing pressure support system.

Those skilled in the art can further appreciate that accessories typically used with a conventional pressure support system or ventilator, such as a humidifier, heater, aspirating, catheter, lavage catheter, insulation catheter, and other such elements can also be used in conjunction with the pressure support system of the present invention. While the flow/ volume sensing assembly of the present invention has been described above as operating in a CPAP, bi-level, or auto-titration type of pressure support mode, it can be appreciated that such a sensing assembly can be used in conjunction with any type of pressure support or ventilatory system where the flow and/or volume of fluid is to be measured.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A pressure support system comprising:
   a gas carrying conduit having a first end adapted to receive breathing gas from a gas source and a second end;
   a pressure generator disposed at a first location along the conduit for generating a flow of breathing gas within the conduit;
   a first port defined in the conduit at a second location;
   a second port defined in the conduit at a third location, wherein the conduit defines a tortuous path between the second location and the third location so as to induce a pressure differential in the flow of breathing gas between the second location and the third location without providing a flow restricting element in the conduit between the second location and the third location, and
   a sensor associated with the first port and the second port adapted to measure a characteristic of the breathing gas in the conduit resulting from the pressure differential and to output a signal indicative thereof.

2. A system according to claim 1, further comprising a processing unit adapted to receive the signal and to determine, based thereon, a flow of the breathing within the conduit, a volume of breathing gas passing through the conduit, or both, as the characteristic of the breathing gas.

3. A system according to claim 2, wherein the sensor is a mass flow sensor that measures a slip-stream flow of gas through the sensor, and wherein the processor determines, based on the slip-stream flow, the flow of the breathing gas in the conduit, the volume of breathing gas passing through the conduit over a predetermined period of time, or both.

4. A system according to claim 2, wherein the sensor is a pressure sensor that measures the pressure differential, and wherein the processor determines, based on the pressure differential, the flow of the breathing gas in the conduit, the volume of breathing gas passing through the conduit over a predetermined period of time, or both.

5. A system according to claim 1, wherein the pressure generator comprises:
   an impeller;
   a housing in which the impeller is disposed; and
   a motor adapted to drive the impeller.

6. A system according to claim 1, further comprising a pressure controller associated with the conduit for controlling the flow of breathing gas by venting gas from the conduit downstream of the pressure generator.

7. A system according to claim 1, further comprising means for controlling the pressure generator by controlling an operating speed of the pressure generator.

8. A system according to claim 1, further comprising a patient circuit having a first end coupled to the second end of the conduit for carrying the flow of breathing gas to a patient, and a patient interface coupled to the second end of the patient circuit for communicating the flow of breathing gas with an airway of a patient.

9. A system according to claim 1, wherein the second location and the third location are upstream of the first location in the conduit.

10. A system according to claim 1, wherein the second location and the third location are downstream of the first location in the conduit.

11. A system according to claim 1, further comprising a noise suppression material disclosed on an inside wall of the conduit for suppressing noise generated by operation of the pressure generator.

12. A system according to claim 1, further comprising:
   a processing unit adapted to receive the signal and to determine, based thereon, a flow of the breathing within the conduit, a volume of breathing gas passing through the conduit, or both, as the characteristic of the breathing gas; and
   pressure regulating means for controlling a pressure of the flow of breathing gas delivered to a patient from the second end of the conduit based on a control signal provided by the processing unit.

13. A system according to claim 12, wherein the pressure regulating means includes at least one of:
   (1) a valve, associated with the conduit, for venting gas from the conduit according to the control signal from the processing unit; and
   (2) a variable speed motor provided in the pressure generator, wherein a speed of the motor is adjustable according to the control signal from the processing unit.

14. A method of providing pressure support comprising:
   providing a gas carrying conduit having a first end adapted to receive breathing gas from a gas source and a second end;
   generating a flow of breathing gas within the conduit via a pressure generator disposed at a first location along the conduit;
   providing a first port in the conduit at a second location;
   providing a second port in the conduit at a third location, wherein the conduit defines a tortuous path between the second location and the third location so as to induce a pressure differential in the flow of breathing gas between the second location and the third location without providing a flow restricting element in the conduit between the second location and the third location, and
   measuring, via a sensor associated with the first port and the second port, a characteristic of the breathing gas in the conduit resulting from the pressure differential and outputting a signal indicative thereof.

15. A method according to claim 14, further comprising determining, based on the signal, a flow of the breathing within the conduit, a volume of breathing gas passing through the conduit, or both, as the characteristic of the breathing gas.

16. A method according to claim 15, wherein the sensor is a mass flow sensor, and wherein measuring a characteristic of the breathing gas includes measuring a slip-stream flow of gas passing through the sensor.

17. A method according to claim 15, wherein the sensor is a pressure sensor, and wherein measuring a characteristic of the breathing gas includes measuring the pressure differential via the pressure sensor.

18. A method according to claim 14, wherein the pressure generator comprises an impeller, a housing in which the impeller is disposed, and a motor adapted to drive the impeller, and wherein generating a flow of breathing gas includes rotating the impeller within the housing via the motor.

19. A method according to claim 14, further comprising controlling the flow of breathing gas by venting gas from the conduit downstream of the pressure generator.

20. A method according to claim 14, further comprising controlling an operating speed of the pressure generator.

21. A method according to claim 14, further comprising carrying the flow of breathing gas to a patient via a patient circuit having a first end coupled to the second end of the conduit, and communicating the flow of breathing gas with an airway of such a patient via a patient interface coupled to the second end of the patient circuit.

22. A method according to claim 14, wherein the second location and the third location are upstream of the first location in the conduit.

23. A method according to claim 14, wherein the second location and the third location are downstream of the first location in the conduit.

24. A method according to claim 14, further comprising suppressing noise generated by operation of the pressure generator by providing a noise suppression material on an inside wall of the conduit.

25. A method according to claim 14, further comprising:
   determining, based on the signal from the sensor, a flow of the breathing within the conduit, a volume of breathing gas passing through the conduit, or both, as the characteristic of the breathing gas; and
   controlling a pressure of the flow of breathing gas delivered to a patient from the second end of the conduit based on a control signal provided by the processing unit.

26. A method according to claim 25, wherein controlling the pressure of the flow of breathing gas includes at least one of:
   venting gas from the conduit according to the control signal from the processing unit; and
   adjusting an operating speed of the pressure generator according to the control signal from the processing unit.

* * * * *